US00PP15893P2

(12) United States Plant Patent
Westhoff

(10) Patent No.: US PP15,893 P2
(45) Date of Patent: Jul. 26, 2005

(54) *SCAEVOLA* PLANT NAMED 'WESSCAEAM'

(50) Latin Name: *Scaevola aemula*
Varietal Denomination: Wesscaeam

(75) Inventor: Heinrich Westhoff, Südlohn (DE)

(73) Assignee: Josef und Heinrich Westhoff Gartenbau-Spezialkulturen, Südlohn (DE)

( * ) Notice: Subject to any disclaimer, the term of this patent is extended or adjusted under 35 U.S.C. 154(b) by 9 days.

(21) Appl. No.: 10/920,828

(22) Filed: Aug. 18, 2004

(51) Int. Cl.[7] ..... A01H 5/00
(52) U.S. Cl. ..... Plt./363
(58) Field of Search ..... Plt./363

(56) References Cited

U.S. PATENT DOCUMENTS

PP9,867 P * 4/1997 Westhoff ..... Plt./363
PP10,201 P * 1/1998 Marriott ..... Plt./363
PP12,099 P2 * 9/2001 Westhoff ..... Plt./363
PP15,086 P2 * 8/2004 Westhoff ..... Plt./363

OTHER PUBLICATIONS

UPOV ROM GTITM Computer Database GTI Jouve Retrieval Software 2004/04 Citation for Wesscaeam.*

* cited by examiner

*Primary Examiner*—Kent Bell
*Assistant Examiner*—W. C. Haas

(74) *Attorney, Agent, or Firm*—C. A. Whealy

(57) ABSTRACT

A new and distinct cultivar of *Scaevola* plant named Wesscaeam, characterized by its spreading to cascading and uniformly rounded plant habit; freely branching habit; dense and bushy plant form; freely flowering habit; and solid violet-colored flowers.

1 Drawing Sheet

Botanical designation: *Scaevola aemula.*
Variety denomination: 'Wesscaeam'.

BACKGROUND OF THE INVENTION

The present Invention relates to a new and distinct cultivar of *Scaevola* plant, botanically known as *Scaevola aemula* and hereinafter referred to by the cultivar name 'Wesscaeam'.

The new *Scaevola* is a product of a planned breeding program conducted by the Inventor in Südlohn, Germany. The new *Scaevola* originated from a cross-pollination made by the Inventor of a proprietary selection of *Scaevola* identified as code number 99Sc0, not patented, as the female, or seed, parent with a proprietary selection of *Scaevola* identified as code number 99Sc72, not patented, as the male, or pollen, parent. The new *Scaevola* was discovered and selected by the Inventor in 2001 in a controlled environment in Südlohn, Germany as a single flowering plant within the resulting progeny from the stated cross-pollination.

Asexual reproduction of the new cultivar by terminal cuttings at Südlohn, Germany since 2001, has shown that the unique features of this new *Scaevola* are stable and reproduced true to type in successive generations.

SUMMARY OF THE INVENTION

The new cultivar has not been observed under all possible environmental conditions. The phenotype may vary somewhat with variations in environment such as temperature and light intensity, without, however, any variance in genotype.

The following characteristics have been repeatedly observed and are determined to be the basic characteristics of 'Wesscaeam' which distinguish 'Wesscaeam' as a new and distinct cultivar:

1. Spreading to cascading and uniformly rounded plant habit.
2. Freely branching habit; dense and bushy plant form.
3. Freely flowering habit.
4. Solid violet-colored flowers.

Plants of the new *Scaevola* can be compared to plants of the female parent selection. In side-by-side comparisons conducted by the Inventor in Südlohn, Germany, plants of the new *Scaevola* and the female parent selection differed in the following characteristics:

1. Plants of the new *Scaevola* were more cascading and not as compact as plants of the female parent selection.
2. Stems of plants of the new *Scaevola* were glabrous whereas stems of plants of the female parent selection were slightly pubescent.
3. Plants of the new *Scaevola* were more freely flowering than plants of the female parent selection.

Plants of the new *Scaevola* can be compared to plants of the male parent selection. In side-by-side comparisons conducted by the Inventor in Südlohn, Germany, plants of the new *Scaevola* and the male parent selection differed in the following characteristics:

1. Plants of the new *Scaevola* were more freely branching than plants of the male parent selection.
2. Plants of the new *Scaevola* were more freely flowering than plants of the male parent selection.
3. Plants of the new *Scaevola* had larger flowers than plants of the male parent selection.

Plants of the new *Scaevola* can be compared to plants of the cultivar Brilliant, disclosed in U.S. Plant Pat. No. 12,099. In side-by-side comparisons conducted by the Inventor in Südlohn, Germany, plants of the new *Scaevola* and the cultivar Brilliant differed in the following characteristics:

1. Plants of the new *Scaevola* had longer lateral branches and longer internodes than plants of the cultivar Brilliant.
2. Stems of plants of the new *Scaevola* were glabrous whereas stems of plants of the cultivar Brilliant were pubescent.
3. Plants of the new *Scaevola* were more freely flowering than plants of the cultivar Brilliant.
4. Plants of the new *Scaevola* and the cultivar Brilliant differed in flower color.

Plants of the new *Scaevola* can also be compared to plants of the cultivar Fancy, disclosed in U.S. Plant Pat. No. 9,867. In side-by-side comparisons conducted by the Inventor in Südlohn, Germany, plants of the new *Scaevola* and the cultivar Fancy differed in the following characteristics:

1. Plants of the new *Scaevola* were more cascading than plants of the cultivar Fancy.
2. Plants of the new *Scaevola* were more freely flowering than plants of the cultivar Fancy.
3. Plants of the new *Scaevola* and the cultivar Fancy differed in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Scaevola*.

The photograph at the bottom of the sheet comprises a side perspective view of a typical plant of 'Wesscaeam' grown in a container.

The photograph at the top of the sheet is a close-up view of typical flowers of 'Wesscaeam'.

DETAILED BOTANICAL DESCRIPTION

Plants used in the aforementioned photographs and for the following description were grown under conditions which closely approximate commercial production conditions during the spring and summer in a glass-covered greenhouse in Südlohn, Germany. Plants were about 35 weeks from planting rooted cuttings in 12-cm containers. During the production of the plants, the day temperatures ranged from 20 to 25° C. and night temperatures ranged from 16 to 18° C. Plants were pinched about three to four weeks after planting and then given a second pinch about four weeks later.

In the following description, color references are made to The Royal Horticultural Society Colour Chart, 2001 Edition, except where general terms of ordinary dictionary significance are used.

Botanical classification: *Scaevola aemula* cultivar Wesscaeam.

Parentage:

*Female parent.*—Proprietary selection of *Scaevola aemula* identified as 99Sc0, not patented.

*Male parent.*—Proprietary selection of *Scaevola aemula* identified as 99Sc72, not patented.

Propagation:

*Type cutting.*—Terminal cuttings.

*Time to develop roots.*—About four weeks at 22° C.

*Root description/habit.*—Fine, fibrous and freely branching.

Plant description:

*Plant form and growth habit.*—Annual container and garden plant. Spreading to cascading and uniformly rounded plant habit; eventually plants become roughly spherical in shape. Suitable for hanging basket, window box and patio containers. Freely branching with lateral branches potentially forming at every vegetative leaf axil when pinched; dense and bushy plant form. Vigorous growth habit.

*Plant height* (*soil level to top of plant plane*).—About 12 to 20 cm.

*Plant length* (*soil level to apices of lateral branches*).—About 80 to 120 cm.

*Stem description.*—Lateral branch length: About 30 to 50 cm. Lateral branch diameter: About 2.3 mm. Main branch length: About 67 to 115 cm. Main branch diameter: About 4.8 mm. Internode length: About 2.5 to 5.4 cm. Texture: Smooth, glabrous. Color: 144A to 146A.

*Foliage description.*—Arrangement: Alternate, simple; sessile. Length: About 6 to 10 cm. Width: About 1.6 to 3.3 cm. Shape: Oblanceolate. Apex: Acute. Base: Attenuate. Margin: Irregularly serrated, slightly serrated towards base and more strongly serrated towards apex. Texture, upper and lower surfaces: Pubescent, rough and somewhat leathery. Venation pattern: Pinnate. Color: Developing and fully expanded leaves, upper surface: 147A. Developing and fully expanded leaves, lower surface: 147B. Venation, upper surface: 147A. Venation, lower surface: Slightly darker than 144A.

Flower description:

*Flower type and shape.*—Zygomorphic, semi-circular, fan-shaped flowers with five petals fused at the base to form a tubular flower throat. Flower throat open along the upper surface exposing reproductive organs. Flowers not persistent. No fragrance detected.

*Flower arrangement and quantity.*—Solitary flowers arise from leaf axils with one flower per axil. Flowers held outwardly on upturned lateral apices. Freely flowering, typically about six to ten open flowers per inflorescence.

*Flowering time.*—Plants flower continuously from May until frost. Flowers typically last about one week on the plant.

*Flower buds.*—Shape: Lanceolate. Length: About 7 to 18 mm. Diameter: About 1.8 to 3 mm. Color: 138B becoming closer to 144C overlain with 187C with development.

*Perianth.*—Aspect: Fan-shaped, flat. Length, fan: About 3.2 cm. Width, fan: About 2.4 cm. Flower throat diameter: About 3.7 mm. Flower tube length: About 1.4 cm. Flower tube diameter, base: About 2 mm.

*Petals.*—Quantity: Five, fused at base. Shape: Lanceolate to ovate. Apex: Cuspidate. Margin: Entire. Length, above tube: About 1.5 cm. Width, above tube: About 5.7 mm. Texture, upper and lower surfaces: Smooth; flower throat, whiskered. Color: When opening, upper surface: N87A. When opening, lower surface and tube: N87B. Fully opened, upper surface: N87B; venation, 90D; color becoming closer to N87B to N87C with development. Fully opened, lower surface: N87C; venation, 85D. Throat: 6B; venation, N79A. Tube: 145C; venation, 200C.

*Sepals.*—Quantity and arrangement: One large sepal, two smaller sepals lateral to larger sepal. Length: Larger sepal, about 1.5 to 1.7 cm; lateral sepals, about 7.5 mm. Width: Larger sepal, about 7.7 mm; lateral sepals, about 1.2 mm. Shape: Larger sepal, ovate to rhomboid; lateral sepals, acicular, needle-like. Apex: Acute. Margin: Entire. Texture, upper and lower surfaces: Leathery, slightly pubescent. Color, upper surface: 147A. Color, lower surface: 147B.

*Reproductive organs.*—Androecium: Stamen quantity per flower: About five. Anthers: Shape: Ovate. Length: About 2 mm. Diameter: About 1 mm. Color: 18B. Filament length: About 5 mm. Pollen: Sparse. Pollen color: 18B. Gynoecium: Pistil quantity per flower: One. Pistil length: About 1.5 cm. Style length: About 9 mm. Style color: Towards the base, 145D; towards the apex, 187A. Stigma shape: Elongate. Stigma color: 155A to 157A; pubescence, 187A. Ovary color: 144A.

*Seed/fruit.*—Seed and fruit production has not been observed.

Disease/pest resistance: Plants of the new *Scaevola* have not been noted to be resistant to pathogens and pests common to *Scaevola.*

Temperature tolerance: Plants of the new *Scaevola* have been observed to be tolerant to temperatures ranging from 2 to 30° C.

It is claimed:

1. A new and distinct *Scaevola* plant named Wesscaeam, as illustrated and described.

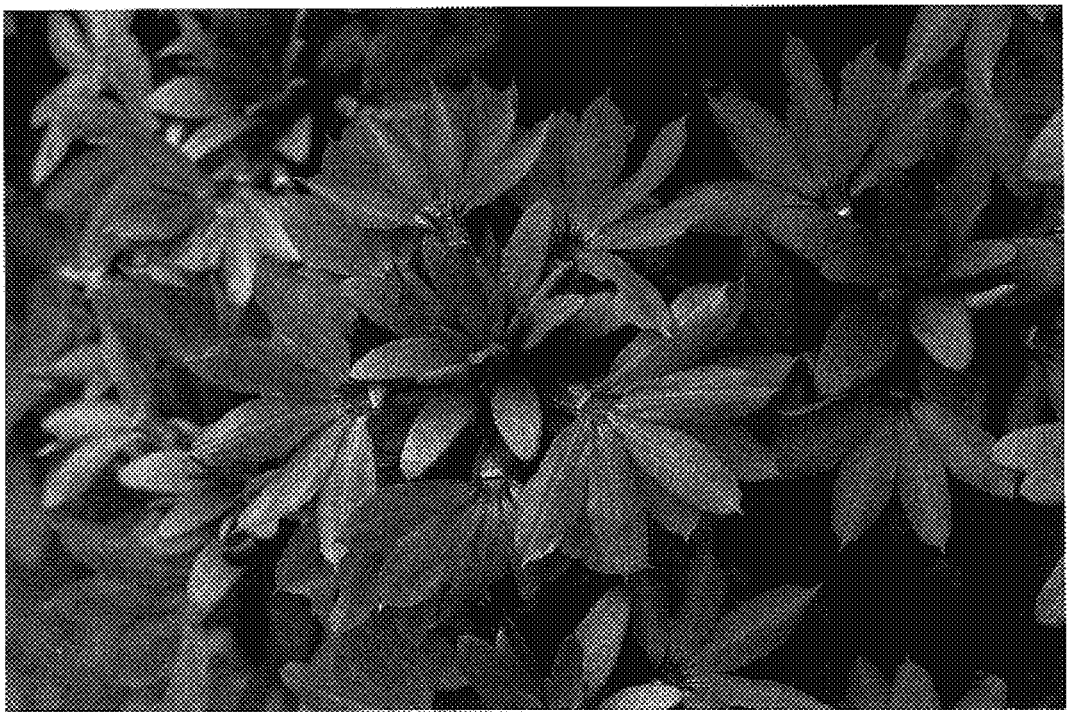
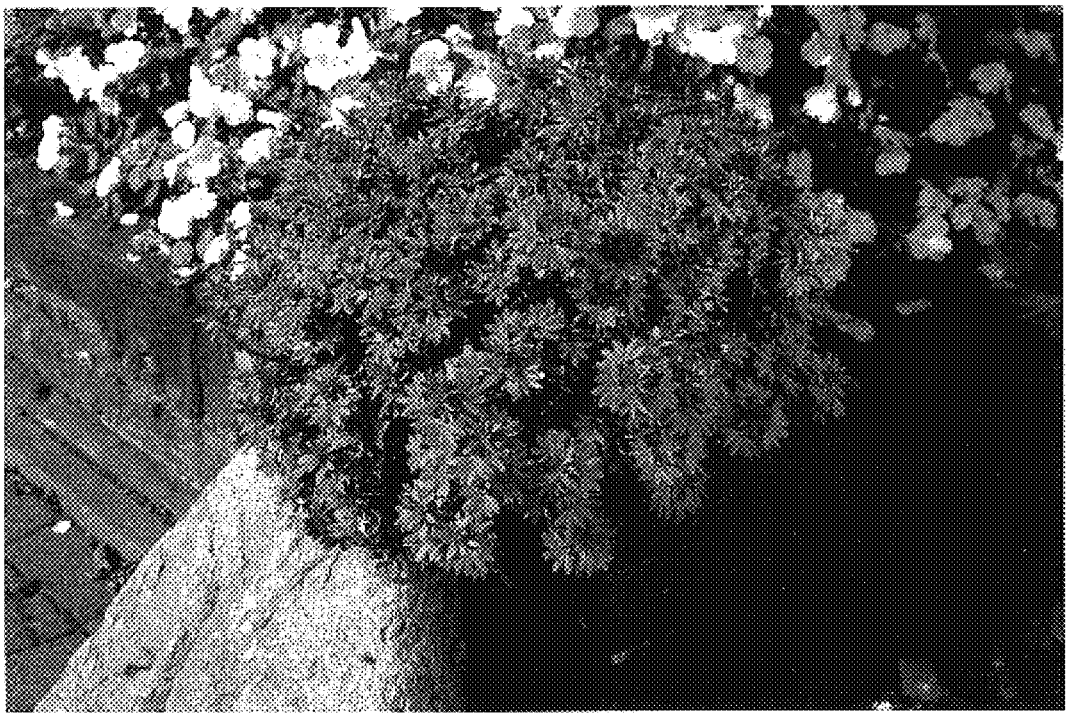

* * * * *